US012648856B2

(12) United States Patent
 Yang et al.

(10) Patent No.: US 12,648,856 B2
(45) Date of Patent: Jun. 9, 2026

(54) MUSCLE FUNCTION PRESERVATION TYPE TOTAL TEMPOROMANDIBULAR JOINT PROSTHESIS

(71) Applicant: SHANGHAI NINTH PEOPLE'S HOSPITAL, SHANGHAI JIAOTONG UNIVERSITY SCHOOL OF MEDICINE, Shanghai (CN)

(72) Inventors: Chi Yang, Shanghai (CN); Jisi Zheng, Shanghai (CN); Zixian Jiao, Shanghai (CN); Minjie Chen, Shanghai (CN); Wenbo Jiang, Shanghai (CN)

(73) Assignee: Shanghai Ninth People's Hospital, Shanghai JiaoTong University School of Medicine, Shanghai (CN)

( * ) Notice: Subject to any disclaimer, the term of this patent is extended or adjusted under 35 U.S.C. 154(b) by 638 days.

(21) Appl. No.: 18/022,253

(22) PCT Filed: Nov. 18, 2020

(86) PCT No.: PCT/CN2020/129722
 § 371 (c)(1),
 (2) Date: Mar. 20, 2023

(87) PCT Pub. No.: WO2022/036899
 PCT Pub. Date: Feb. 24, 2022

(65) Prior Publication Data
 US 2023/0404763 A1 Dec. 21, 2023

(30) Foreign Application Priority Data

Aug. 21, 2020 (CN) ......................... 202010850275.X
Aug. 21, 2020 (CN) ......................... 202021764320.1

(51) Int. Cl.
 *A61F 2/30* (2006.01)
 *A61B 17/80* (2006.01)

(52) U.S. Cl.
 CPC ........ *A61F 2/3099* (2013.01); *A61B 17/8071* (2013.01); *A61F 2002/30991* (2013.01); *A61F 2002/30993* (2013.01)

(58) Field of Classification Search
 CPC .......... A61F 2/3099; A61F 2002/30991; A61F 2002/30993; A61F 2/30942;
 (Continued)

(56) References Cited

U.S. PATENT DOCUMENTS

| 4,917,701 A | 4/1990 | Morgan |
| 2019/0192302 A1 | 6/2019 | Mommaerts |

FOREIGN PATENT DOCUMENTS

| CN | 207125817 U | 3/2018 |
| CN | 108720969 A | 11/2018 |

(Continued)

*Primary Examiner* — Yashita Sharma
(74) *Attorney, Agent, or Firm* — IPRTOP LLC

(57) ABSTRACT

A muscle function preservation type total temporomandibular joint prosthesis includes an articular fossa member (1) and an articular head member (2) abutting against the articular fossa member (1). The articular head member (2) includes a mandibular trailing edge fixing plate (21), a sigmoid notch fixing plate (22) and an articular head portion (23). The mandibular trailing edge fixing plate (21) is connected to a bottom end of the articular head portion (23) and extends downwards, and has a plate-shaped structure and includes a mandibular-trailing-edge-surface attaching surface. The sigmoid notch fixing plate (22) protrudes from one side of the mandibular trailing edge fixing plate (21) and extends in a direction away from the mandibular trailing edge fixing plate (21), and has a plate-shaped structure and includes a mandibular-ramus-proximal-sigmoid-notch-portion attaching surface.

10 Claims, 6 Drawing Sheets

(58) Field of Classification Search
CPC .. A61F 2002/30011; A61F 2002/30578; A61F
2002/30784; A61F 2002/3092; A61F
2002/30948; A61F 2002/30985; A61F
2/30; A61B 17/8071
See application file for complete search history.

(56) References Cited

FOREIGN PATENT DOCUMENTS

| | | | |
|---|---|---|---|
| CN | 111839817 | A | 10/2020 |
| EP | 0203719 | A1 | 12/1986 |
| GB | 2480682 | A | 11/2011 |
| JP | 11146889 | A | 6/1999 |

MUSCLE FUNCTION PRESERVATION TYPE TOTAL TEMPOROMANDIBULAR JOINT PROSTHESIS

CROSS REFERENCE TO RELATED PATENT APPLICATION

The present application is the US national stage of PCT/CN2020/129722 filed on 2020 Nov. 18, which claims the priorities of the CN 202010850275.X filed on 2020 Aug. 21 and CN 202021764320.1 filed on 2020 Aug. 21, which applications are incorporated herein by reference.

TECHNICAL FIELD

The present disclosure relates to the field of medical devices, in particular, to a muscle function preservation type total temporomandibular joint prosthesis.

BACKGROUND

A temporomandibular joint is the only joint of a maxillofacial region which is connected to left and right regions, has rotation and sliding motions, and is one of the most complex joints of a human body anatomically and motionally. Temporomandibular joint disease is a common and frequently-occurring disease, and includes articular region pain, restriction of mouth opening, occlusion disorders, difficulties in mandibular movement and function and the like, which seriously affects functions of chewing, language and the like of patients and even endangers life of patients. Lesion joints need to be removed for diseases such as late temporomandibular joint osteoarthropathy, severe idiopathic condylar absorption, ankylosing spondylitis, comminuted fracture, partial joint tumors and the like, and a total temporomandibular joint (TMJ) is reconstructed using an autologous or allogeneic tissue so as to recover shape and function of the joint to a maximum extent. Using a total TMJ prosthesis is one of effective methods for restoring the shape and function of the joint. Currently, international mainstream products are products of standard Zimmer Biomet and customized TMJ Concepts. However, these two prostheses are applied less domestically due to a poor fit to a joint structure of Chinese people and a high price (70-150 thousand RMB per side) respectively. A product with the patent grant publication No. CN 205626192 U has a good safety and effectiveness proved by a clinical preliminary experiment. The three prostheses mainly focus on recovery of a joint function, a condyle is completely resected in an operation, and an attachment of a lateral pterygoid muscle on a joint is lost. Meanwhile, a mandibular handle is attached to a mandibular ramus surface, a partial attachment of a masseter is lost, such that a patient after an operation has complications of lateral movement limitation, severe mandibular deviation during mouth opening, and masticatory weakness.

SUMMARY

The present disclosure provides a muscle function preservation type total temporomandibular joint prosthesis.

The prosthesis at least includes from top to bottom: an articular fossa member and an articular head member abutting against the articular fossa member. The articular fossa member includes a zygomatic arch retaining portion for being fixed to a zygomatic arch of a human body and an articular fossa portion connected with the zygomatic arch retaining portion. The articular head member includes a mandibular trailing edge fixing plate, a sigmoid notch fixing plate and an articular head portion. The articular head portion has a shape of a complete or partial condyle and abuts against the articular fossa member. The mandibular trailing edge fixing plate is connected to a bottom end of the articular head portion and extends downwards, and has a plate-shaped structure and includes a mandibular-trailing-edge-surface attaching surface which fits snugly with a surface of a trailing edge of a mandible of the human body. The sigmoid notch fixing plate protrudes from one side of the mandibular trailing edge fixing plate and extends in a direction away from the mandibular trailing edge fixing plate, and has a plate-shaped structure and includes a mandibular-ramus-proximal-sigmoid-notch-portion attaching surface which fits snugly with a proximal sigmoid notch portion of a mandibular ramus of the human body.

As described above, the muscle function preservation type total temporomandibular joint prosthesis of the present disclosure has the following beneficial effects:

The muscle function preservation type total temporomandibular joint prosthesis of the present disclosure can effectively restore a normal anatomical structure of TMJ, can restore functions of chewing, speech, movement, etc. of a patient, only restores an articular surface, and preserves most of a joint bone structure and an attachment and a function of a lateral pterygoid muscle, and solves a problem of a mandibular deviation of the patient. The prosthesis preserves most of a masseter attachment region and functions and solves a problem of masticatory weakness of the patient. The prosthesis is conductive for stress conduction and distribution of a mandible, can effectively avoid stress concentration of the prosthesis and achieves a long-term effective fixation. The prosthesis can quickly and firmly combine with a bone to maintain a long-term stability of the prosthesis. The prosthesis is fine in design, reduces surgical wounds, shortens surgery time and reduces a surgical difficulty. The present disclosure personally restores a temporomandibular joint, preserves an attachment of a lateral pterygoid muscle and a masseter, and has remarkable effects on a normal recovery of a temporomandibular joint function, a mandibular movement and a masticatory function.

REFERENCE NUMERALS OF ELEMENTS

Figure 1:
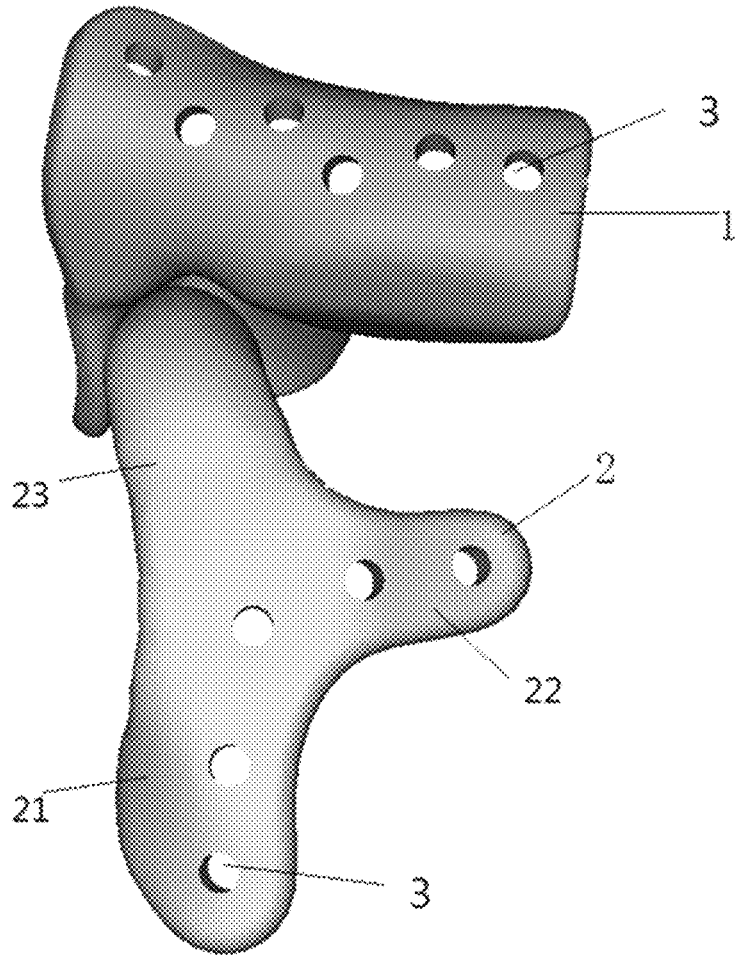
FIG. 1 is a structure diagram of a muscle function preservation type total temporomandibular joint prosthesis according to an embodiment of the present disclosure.

1 Articular fosse member
11 Articular fosse portion
111 Bone surface
112 Motion function surface
12 Zygomatic arch retaining portion
2 Articular head member
21 Mandibular trailing edge fixing plate
22 Sigmoid notch fixing plate
23 Articular head portion
231 Bending portion
3 Fixing nail hole
A Lateral pterygoid muscle attachment region
B Masseter attachment region
C Extending downward part of articular fossa portion
D Bending part of mandibular trailing edge fixing plate

DETAILED DESCRIPTION

Implementations of the present disclosure are illustrated by a particular embodiment below, and other advantages and effects of the present disclosure will become apparent for those skilled in the art from the disclosure of the description.

Refer to FIGS. 1 to 5b. It should be known that the structure, scale, size, and the like shown in the drawings of the description are only used to match the content disclosed in the description and for those skilled in the art to understand and read, which are not used to limit the limitations for implementing the present disclosure and thus are not technically substantial. Any structural modification, scaling relation change, or size adjustment made without affecting the effects and objectives that can be achieved by the present disclosure shall fall within the scope that can be encompassed by the technical content disclosed in the present disclosure. Moreover, as used herein, the terms such as "upper", "bottom", "left" "right", "middle" and "a/an" are merely employed for ease of description, and not intended to limit the scope of the present disclosure, and the change or adjustment of the relative relationships shall be deemed as falling within the scope of the present disclosure without substantial alteration of technical contents.

The personalized fit described in the present application refers to that a shape of one side of a prosthesis used to fit a bone surface is adapted to a shape of an autologous bone of different patients, so as to achieve a good fit effect.

Figure 2:
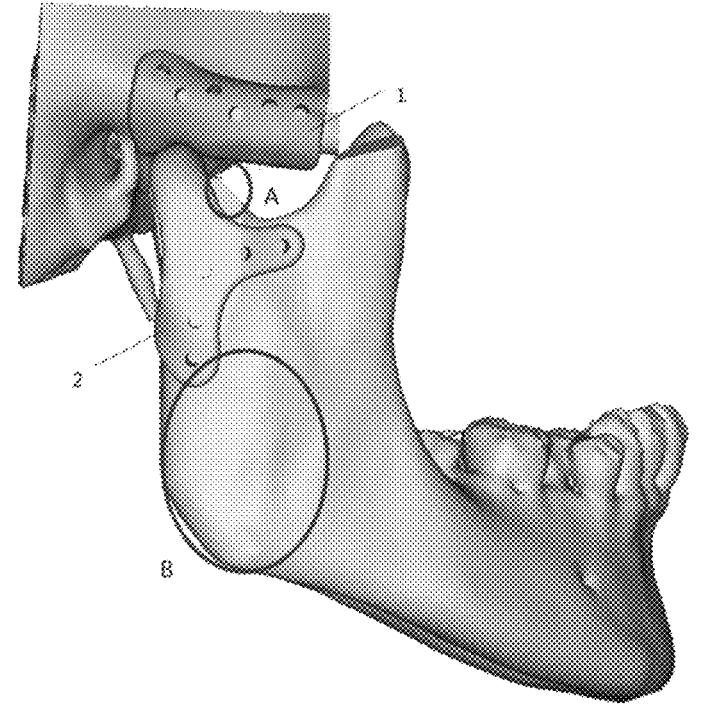
FIG. 2 is a use state diagram of a muscle function preservation type total temporomandibular joint prosthesis according to an embodiment of the present disclosure.
Figure 3A:
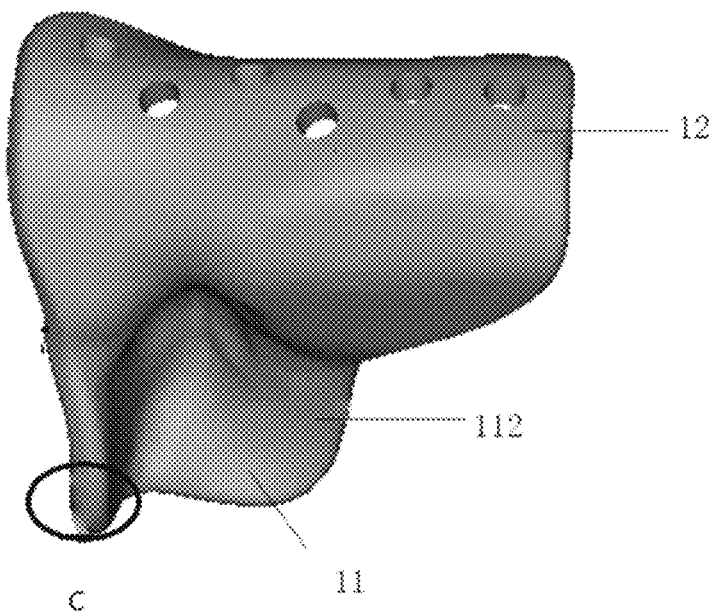
FIG. 3a is a front view of an articular fossa member of a muscle function preservation type total temporomandibular joint prosthesis according to an embodiment of the present disclosure.
Figure 4A:
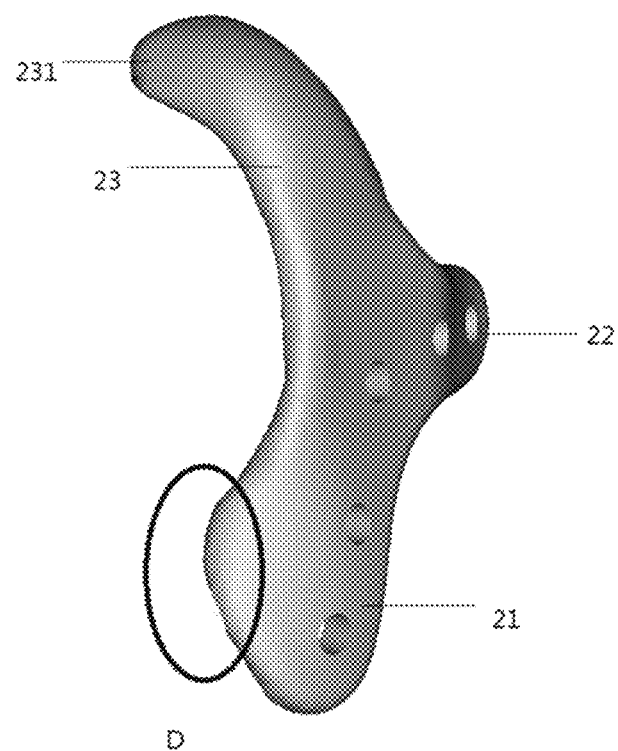
FIG. 4a is a lateral view of an articular head member of a muscle function preservation type total temporomandibular joint prosthesis according to an embodiment of the present disclosure.
Figure 4B:
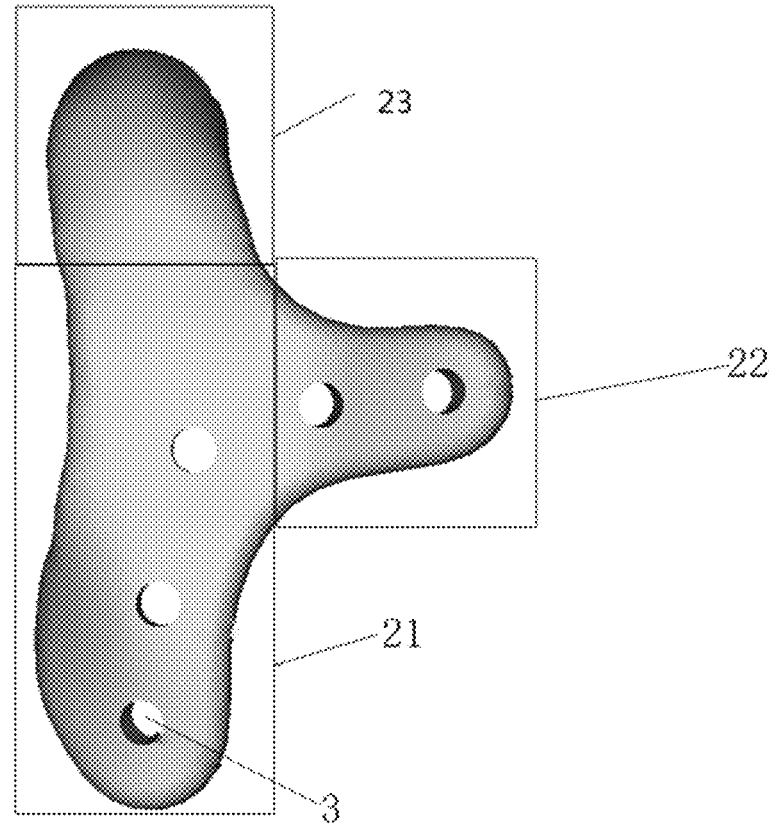
FIG. 4b is a front view of an articular head member of a muscle function preservation type total temporomandibular joint prosthesis according to an embodiment of the present disclosure.

As shown in FIG. 1, a muscle function preservation type total temporomandibular joint prosthesis provided by an embodiment of the present disclosure at least includes from top to bottom: an articular fossa member 1 and an articular head member 2 abutting against the articular fossa member 1; as shown in FIG. 3a, the articular fossa member 1 includes a zygomatic arch retaining portion 12 for being fixed to a zygomatic arch of a human body and an articular fossa portion 11 connected with the zygomatic arch retaining portion 12; as shown in a division in a box of FIG. 4b, the articular head member 2 includes a mandibular trailing edge fixing plate 21, a sigmoid notch fixing plate 22 and an articular head portion 23. The articular head portion 23 has a shape of a complete or partial condyle and abuts against the articular fossa member 1. As shown in FIG. 1 and FIG. 2, a human body face is used as a front, and the mandibular trailing edge fixing plate 21 is connected to a bottom end of the articular head portion 23 and extends downwards, and has a plate-shaped structure and includes a mandibular-trailing-edge-surface attaching surface which fits snugly with a surface of a trailing edge of a mandible of the human body. The sigmoid notch fixing plate 22 protrudes from one side of the mandibular trailing edge fixing plate 21 and extends in a direction away from the mandibular trailing edge fixing plate 21, and has a plate-shaped structure and includes a mandibular-ramus-proximal-sigmoid-notch-portion attaching surface which fits snugly with a proximal sigmoid notch portion of a mandibular ramus of the human body.

The articular head member restores a surface of an articular head of the human body and the articular fossa member restores an articular fossa of the human body.

Further, a length of the mandibular trailing edge fixing plate 21 extending downwards from a bottom end of the articular head portion is 25-35 mm; and/or an extending length of the sigmoid notch fixing plate 22 protruding from the mandibular trailing edge fixing plate 21 is 15-25 mm. A lateral pterygoid muscle attachment region and a masseter attachment region (i.e. A and B regions in FIG. 2) are not covered and functions of the lateral pterygoid muscle and the masseter are preserved.

In an example, at a joint of the mandibular trailing edge fixing plate 21 and the sigmoid notch fixing plate 22, a width of the mandibular trailing edge fixing plate 21 is 5-15 mm, and/or a width of the sigmoid notch fixing plate 22 is 5-15 mm. The lateral pterygoid muscle attachment region and the masseter attachment region (i.e. A and B regions in FIG. 2) are not covered and functions of the lateral pterygoid muscle and the masseter are preserved.

The width of the mandibular trailing edge fixing plate 21 refers to an extending distance of a direction perpendicular to a downward extending direction of the mandibular trailing edge fixing plate 21 from a bottom end of the articular head portion.

The width of the sigmoid notch fixing plate 22 refers to an extending distance of a direction perpendicular to an extending direction of the sigmoid notch fixing plate 22 protruding from the mandibular trailing edge fixing plate 21.

In an example, a width of a tail end of the mandibular trailing edge fixing plate 21 is 5-10 mm, and/or a width of a tail end of the sigmoid notch fixing plate 22 is 5-10 mm. The lateral pterygoid muscle attachment region and the masseter attachment region (i.e. A and B regions in FIG. 2) are not covered and functions of the lateral pterygoid muscle and the masseter are preserved.

In an example, a thickness of the mandibular trailing edge fixing plate 21 and the sigmoid notch fixing plate 22 is 2-3 mm, respectively.

In an example, an included angle between an extending direction of the mandibular trailing edge fixing plate 21 and an extending direction of the sigmoid notch fixing plate 22 is 60-90°. The lateral pterygoid muscle attachment region and the masseter attachment region (i.e. A and B regions in FIG. 2) are not covered and functions of the lateral pterygoid muscle and the masseter are preserved.

Optionally, a top end of the articular head portion 23 is a concave-convex bending portion, a proximal bone surface of the articular head portion is a concave surface, a distal bone surface of the articular head portion is a convex surface, and the distal bone surface is in a concave-convex fit with the articular fossa portion 11.

Optionally, a width of the articular head portion 23 is 5-10 mm, and/or a depth of the articular head portion 23 is 10-20 mm. The articular head portion has a size similar to that of a condyle of the human body.

The depth of the articular head portion refers to an extending distance from one end of the articular head portion in contact with the articular fossa member extending downwards to a contact end of the mandibular trailing edge fixing plate.

The width of the articular head portion refers to an extending distance of a direction perpendicular to a direction of the depth of the articular head portion.

Further, as shown in FIG. 4*a*, a side surface of the articular head member 2 fitting snugly with a human body bone is used as an inner surface, a top end of the articular head portion 23 is bent to the inner surface to form a bending portion 231, an outer surface of the bending portion 231 is a cambered surface, such that an inner side of a joint and a neck of the human body are accommodated, and thus an attachment of a lateral pterygoid muscle is preserved. The bending portion is in a concave-convex fit with the articular fossa portion.

Optionally, as shown in D position in FIG. 4*a*, an extending tail end of the mandibular trailing edge fixing plate 21 is bent towards a rear side bone surface of the trailing edge of the mandible of the human body, such that a part of the trailing edge of the mandible is wrapped, thereby positioning the prosthesis.

Figures 4C, 5A:
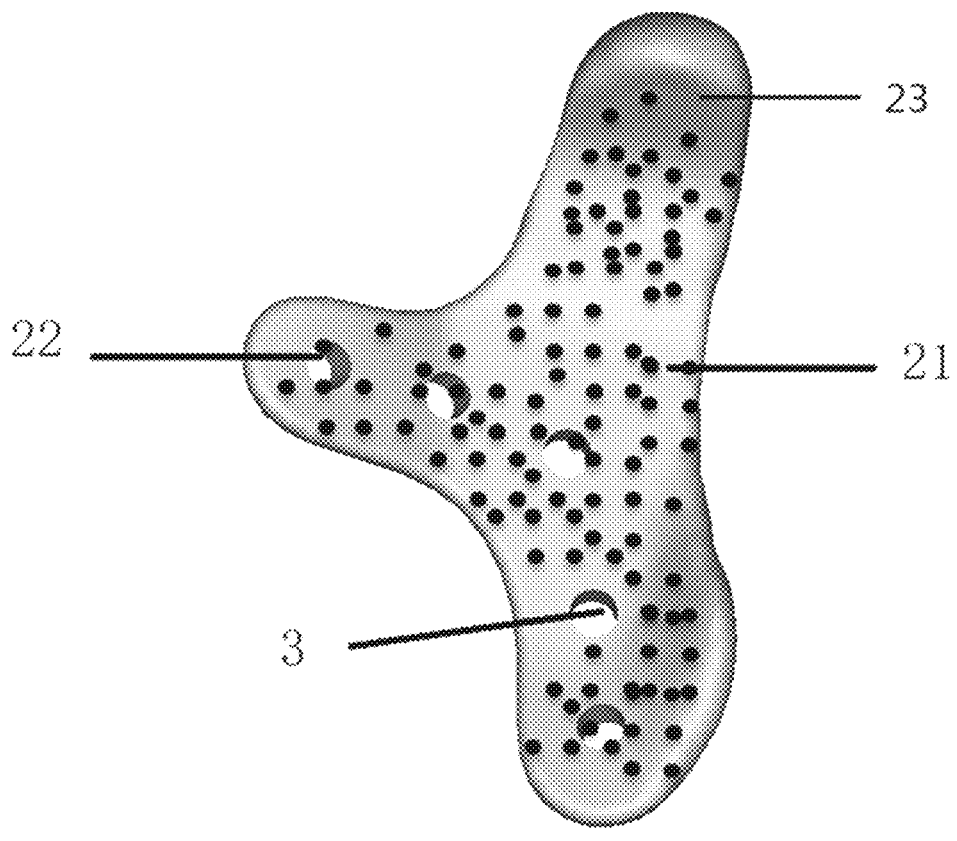
FIG. 4c is a rear view of an articular head member of a muscle function preservation type total temporomandibular joint prosthesis according to an embodiment of the present disclosure.
FIG. 5a is a lateral view of a use state of an articular head member of a muscle function preservation type total temporomandibular joint prosthesis according to an embodiment of the present disclosure.
Figure 5B:
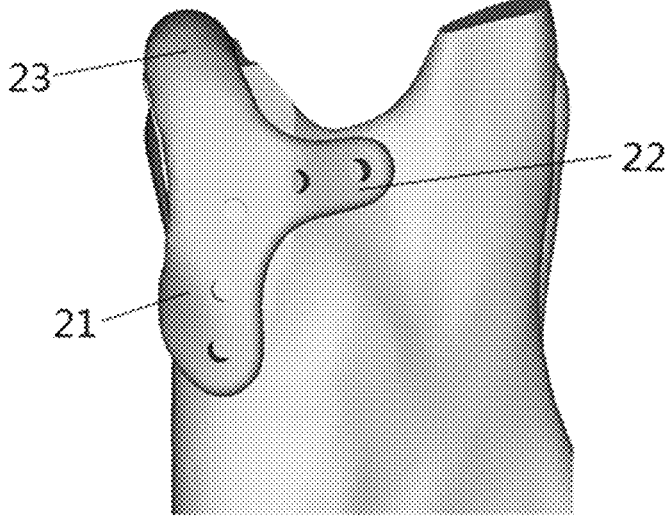
FIG. 5b is a lateral view of a use state of an articular head member of a muscle function preservation type total temporomandibular joint prosthesis according to an embodiment of the present disclosure.

In an example, as shown in FIG. 4*c*, an inner surface of the articular head member may be a rough surface, or has a porous structure containing multiple holes, which is conducive to forming a firm bone combination with an autogenous bone. The porous structure has a thickness of 0.5-1 mm.

Figure 3B:
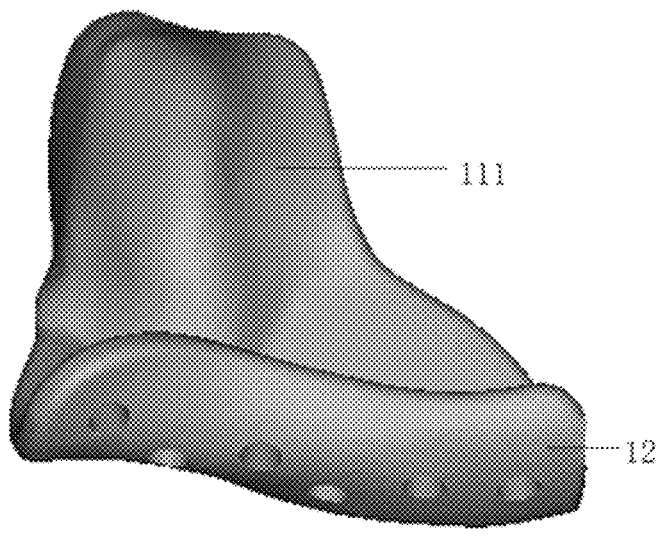
FIG. 3b is a rear view (inverted) of an articular fossa member of a muscle function preservation type total temporomandibular joint prosthesis according to an embodiment of the present disclosure.

Further, as shown in FIG. 3*a* and FIG. 3*b*, the articular fossa portion 11 includes a bone surface 111 and a motion function surface 112, and the bone surface 111 can personally fit snugly with the articular fossa of the human body and an articular tubercle; and the motion function surface 112 abuts against the articular head member 2.

Further, the motion function surface 112 is a concave surface.

Optionally, the motion function surface 112 has a radian of 10-30°. In this radian, the articular fossa portion has a good fit effect with the articular head member.

Optionally, as shown at C position in FIG. 3*a*, a length of a side, far from the sigmoid notch fixing plate 22, of the articular fossa portion 11 is greater than a length of a side near the sigmoid notch fixing plate 22. This design of the articular fossa portion isolates a joint and an auditory meatus of the human body, and prevents the joint from moving backward.

The zygomatic arch retaining portion 12 includes a zygomatic arch attaching surface which can personally fit snugly with a zygomatic arch of the human body, and a thickness of the zygomatic arch retaining portion 12 is 2-3 mm.

Further, plate surfaces of the zygomatic arch retaining portion 12, the mandibular trailing edge fixing plate 21 and the sigmoid notch fixing plate 22 respectively contain fixing nail holes 3.

Optionally, the number of the fixing nail holes of the zygomatic arch retaining portion 12 is 5-7, and the number of the fixing nail holes on the mandibular trailing edge fixing plate 21 and the sigmoid notch fixing plate 22 is 2-3, respectively. Optionally, the nail holes in the mandibular trailing edge fixing plate are arranged at a lower part of a joint of the mandibular trailing edge fixing plate and the sigmoid notch fixing plate 22.

The lower part of the joint of the mandibular trailing edge fixing plate and the sigmoid notch fixing plate 22, and the sigmoid notch fixing plate has a TMJ stress distribution, and an occlusal force can be effectively conducted.

Optionally, an autologous bone of a user may be scanned by CT or MRI scanning, etc., then a three-dimensional model is built, and a 3D printing is performed to obtain the prosthesis or components of the prosthesis.

When in use, the articular fossa member is firstly fixed on the zygomatic arch of the human body through the zygomatic arch retaining portion, and then after the articular head member is fitted with the articular fossa portion, the articular head member is fixed at the mandibular ramus of the human body.

The foregoing embodiments are merely intended to exemplarily explain the principles and effects of the present disclosure, rather than limit the present disclosure. Any person skilled in the art can make modifications or alterations to the foregoing embodiments without departing from the spirit and scope of the present disclosure. Hence, all equivalent modifications or alterations made by those of ordinary skill in the art without departing from the spirit and technical teachings disclosed in the present disclosure shall fall within the scope defined by appended claims to the present disclosure.

What is claimed is:

1. A muscle function preservation type total temporomandibular joint prosthesis, wherein the prosthesis at least comprises from top to bottom: an articular fossa member (1) and an articular head member (2) abutting against the articular fossa member (1); wherein the articular fossa member (1) comprises a zygomatic arch retaining portion (12) for being fixed to a zygomatic arch of a human body and an articular fossa portion (11) connected with the zygomatic arch retaining portion (12); the articular head member (2) comprises a mandibular trailing edge fixing plate (21), a sigmoid notch fixing plate (22) and an articular head portion (23), wherein the articular head portion (23) has a shape of a complete or partial condyle and abuts against the articular fossa member (1); the mandibular trailing edge fixing plate (21) is connected to a bottom end of the articular head portion (23) and extends downwards, and has a plate-shaped structure and comprises a mandibular-trailing-edge-surface attaching surface which is configured to fits snugly with a surface of a trailing edge of a mandible of the human body; and the sigmoid notch fixing plate (22) protrudes from one side of the mandibular trailing edge fixing plate (21) and extends in a direction away from the mandibular trailing edge fixing plate (21), and has a plate-shaped structure and comprises a mandibular-ramus-proximal-sigmoid-notch-portion attaching surface which is configured to fits snugly with a proximal sigmoid notch portion of a mandibular ramus of the human body;

wherein a top end of the articular head portion (23) is a concave-convex bending portion, a proximal bone surface of the articular head portion is a concave surface, a distal bone surface of the articular head portion is a convex surface, and the distal bone surface is in a concave-convex fit with the articular fossa portion (11).

2. The muscle function preservation type total temporomandibular joint prosthesis as in claim 1, wherein a length of the mandibular trailing edge fixing plate (21) extending downwards from the bottom end of the articular head portion (23) is 25-35 mm; and/or an extending length of the sigmoid notch fixing plate (22) protruding from the mandibular trailing edge fixing plate (21) is 15-25 mm.

3. The muscle function preservation type total temporomandibular joint prosthesis as in claim 1, wherein at a joint of the mandibular trailing edge fixing plate (21) and the sigmoid notch fixing plate (22), a width of the mandibular trailing edge fixing plate (21) is 5-15 mm, and/or a width of the sigmoid notch fixing plate (22) is 5-15 mm.

4. The muscle function preservation type total temporomandibular joint prosthesis as in claim 1, wherein a width of an extending tail end of the mandibular trailing edge fixing plate (21) is 5-10 mm, and/or a width of an extending tail end of the sigmoid notch fixing plate (22) is 5-10 mm.

5. The muscle function preservation type total temporomandibular joint prosthesis as in claim 1, wherein a thickness of the mandibular trailing edge fixing plate (21) and the sigmoid notch fixing plate (22) is 2-3 mm, respectively.

6. The muscle function preservation type total temporomandibular joint prosthesis as in claim 1, further comprising one or more of the following features:

a. an extending tail end of the mandibular trailing edge fixing plate (21) is bent towards a rear side bone surface of the trailing edge of the mandible of the human body;

b. an included angle between extending directions of the mandibular trailing edge fixing plate (21) and the sigmoid notch fixing plate (22) is 60-90°;

c. a width of the articular head portion (23) is 5-10 mm and/or a depth of the articular head portion (23) is 10-20 mm; and e. plate surfaces of the zygomatic arch retaining portion (12), the mandibular trailing edge fixing plate (21) and the sigmoid notch fixing plate (22) respectively contain fixing nail holes (3).

7. The muscle function preservation type total temporomandibular joint prosthesis as in claim 1, wherein an inner surface of the articular head member is a rough surface or has a porous structure.

8. The muscle function preservation type total temporomandibular joint prosthesis as in claim 1, wherein the articular fossa portion (11) comprises a bone surface (111) and a motion function surface (112), wherein the bone surface (111) is configured to personally fit snugly with an articular fossa of the human body and an articular tubercle; and the motion function surface (112) abuts against the articular head member (2).

9. The muscle function preservation type total temporomandibular joint prosthesis as in claim 8, wherein the motion function surface (112) is a concave surface.

10. The muscle function preservation type total temporomandibular joint prosthesis as in claim 1, wherein the zygomatic arch retaining portion (12) comprises a zygomatic arch attaching surface which is configured to personally fits snugly with the zygomatic arch of the human body, and a thickness of the zygomatic arch retaining portion (12) is 2-3 mm.

* * * * *